United States Patent [19]

Confer et al.

[11] Patent Number: 4,652,521

[45] Date of Patent: Mar. 24, 1987

[54] METHOD FOR THE EARLY DIAGNOSIS OF BORDETELLA DISEASES AND KIT THEREFOR

[75] Inventors: Dennis L. Confer, St. Paul; John W. Eaton, Minneapolis, both of Minn.

[73] Assignee: Regents of the University of Minnesota, Minneapolis, Minn.

[21] Appl. No.: 707,806

[22] Filed: Mar. 4, 1985

[51] Int. Cl.[4] .................. C12Q 1/04; C12Q 1/00; C12Q 1/16; C12Q 1/06; C12M 1/40; C12M 1/30; C12M 1/24; G01N 33/566

[52] U.S. Cl. .......................................... 435/34; 435/4; 435/35; 435/39; 435/288; 435/295; 435/296; 435/803; 436/501; 436/810

[58] Field of Search ................. 435/29, 34, 35, 39, 435/4, 295, 296, 288, 803; 436/104, 105, 111, 501, 810

[56] References Cited

U.S. PATENT DOCUMENTS 3,368,549  2/1968  Barr et al. ........................... 435/295
4,150,950  4/1979  Takeguchi et al. .................. 435/296

OTHER PUBLICATIONS

Goldhammer et al., *Eur. J. Biochem.*, pp. 605–609 (1981).
Chemical Abstract: 101:222202K, Slungaard et al., *Trans. Assoc. Am. Physicians*, 1983, 96, 401–5.
Moss et al., *J. Recept. Res.* (U.S.), 1984, 4(1–6), pp. 459–474 (abstract).
Goldhammer et al., *Eur. J. Biochem.*, 115(3), 1981, 605–610 (abstract).
Chemical Abstract: 77:161720q, *Biochem. J.*, 1972, 129(1), 113–21, Weller et al.
Manual of Clinical Microbiology, 3rd ed., 1980, p. 991, Lennette et al.
Tao et al, 1969, PNAS, 63:86–92.
Hewlett et al, 1976, American Society of Microbiology, 127:890–898.
Endoh et al, 1980, Microbiology Immunology, 24:95–104.
Wolff et al, 1980, PNAS, 77:3841–3844.

*Primary Examiner*—Esther M. Kepplinger
*Assistant Examiner*—L. Krawczewicz
*Attorney, Agent, or Firm*—Burd, Bartz & Gutenkauf

[57] ABSTRACT

A method for the early diagnosis of Bordetella diseases based on the detection of Bordetella adenylate cyclase and the ability of this enzyme to catalyze the formation of cyclic adenosine monophosphate (cAMP). A sample secretion is taken from a suspected victim of a Bordetella disease (the most common of which in humans is whooping cough) and incubated under conditions to promote the formation of cAMP, which may then be measured as evidence of the presence of the disease. A sample of nasopharyngeal secretions is maintained in a nutrient medium pending assay. An adenylate cyclase assay is made by incubating the sample with adenosine triphosphate (ATP) and the calcium binding protein calmodulin to generate cAMP. The cAMP is measured by any of several known available methods. To facilitate diagnosis, a kit is provided containing the materials necessary for collection of secretion specimens, for storage of specimens pending assay, and transport of specimens to the assay laboratory, and for performing the assay and determining the result.

14 Claims, No Drawings

METHOD FOR THE EARLY DIAGNOSIS OF BORDETELLA DISEASES AND KIT THEREFOR

FIELD OF THE INVENTION

Background of the Invention

This invention is directed to a rapid method for the early diagnosis of Bordetella diseases, the most common of which in humans is whooping cough (*Bordetella pertussis*), and to a kit for facilitating diagnosis. Because whooping cough is the Bordetella disease of greatest interest and concern, most of the experimental work has been directed to its diagnosis. The invention is described with particular reference to whooping cough.

Infection with *Bordetella pertussis* remains a serious health problem. In countries of the world where vaccination is not feasible, whooping cough may cause more than one-half million deaths annually. In the United States and Europe, death from whooping cough is unusual, but morbidity from the infection is high and costly. Furthermore, the incidence of whooping cough is increasing due to a developing vaccine shortage and to public refusal to accept the risks of currently available pertussis vaccines. Whooping cough is, and will remain, a significant health hazard. A principal object of this invention is to facilitate control of this hazard by providing improved methods of detecting *B. pertussis* infection.

Whooping cough is an unusual bacterial infection. Over 90 percent of exposed, susceptible persons will become infected. These persons will be infectious to others for almost three weeks, but their symptoms during this time are indistinguishable from those of the common cold. With the onset of the classical whooping cough phase, infectiousness falls rapidly indicating diminished shedding of viable bacteria. Symptoms during this phase, when morbidity and mortality are highest, are not due to the continued influence of viable organisms as evidenced by the failure of antibiotic therapy to exert any modifying effect.

Thus, to control infectivity and limit the severity of symptoms, infection with *B. pertussis* must be identified early in the catarrhal phase of the illness. The ideal diagnostic test for pertussis should have several features:

(1) Easy specimen collection—The sample should be easily obtained at no risk to the patient with minimal training required by personnel.

(2) Simple sample holding and transport needs—Samples collected in the outpatient clinic must not be subject to stringent holding and transport requirements such that special equipment is necessary or critical time constraints are present.

(3) Rapid sample processing—Parallel processing of samples is necessary to ensure rapid throughput and minimize labor costs. Rapid turnaround time is essential. Diagnostic tests which require special technical skills are not desirable.

(4) High sensitivity and specificity—The test must be sensitive early in the catarrhal phase of infection and specificity of the result is required. The present invention satisfies these criteria.

*Bordetella pertussis* elaborates two potent toxins which disrupt adenosine 3',5'-cyclic monophosphate (cAMP) metabolism in mammalian cells. The first of these, pertussis toxin (also known as lymphocytosis promoting factor, islet activating protein, pertussigen, and others), is a multimeric protein complex which acts on membrane bound adenylate cyclase of the target cell. The substrate for pertussis toxin is a 41,000$M_r$ protein that is part of the regulatory subunit ($N_i$) which effects hormone dependent inhibition of adenylate cyclase activity. When this protein is ADP-ribosylated by pertussis toxin, adenylate cyclase is released from the constraining influence of $N_i$: the response of adenylate cyclase to inhibitor hormones is lost, while the response to stimulators is enhanced. Thus, pertussis toxin enhances the production of intracellular cAMP.

Though less well understood, Bordetella adenylate cyclase is an equally fascinating product of the bacterium. This extracytoplasmic enzyme was first identified in *B. pertussis* vaccines and subsequently in the supernatant fraction of fluid phase organisms. Unusual characteristics of this adenylate cyclase include pronounced heat stability and a high specific activity markedly enhanced by the eukaryotic calcium binding protein, calmodulin. It was hypothesized that Bordetella adenylate cyclase may function as a toxin by insinuating itself into target cells and catalyzing the unregulated formation of intracellular cAMP. The prediction was based, in part, on several unexplained features of the whooping cough syndrome. These included the absence of fever, the lack of an adequate neutrophil response, and a high incidence of secondary bacterial pneumonias. Each of these suggests a serious dysfunction of alveolar macrophages. Furthermore, previous investigations had shown that elevations of intracellular cAMP would impair function of such phagocytic cells and others had already reported severe alveolar macrophage defects in rabbits infected with the related organism, *B. bronchiseptica*.

A number of *B. pertussis* preparations were screened for their ability to directly elevate intracellular cAMP and impair phagocyte function. The predicted activity was reproducibly obtained when cell coats of whole organisms were solubilized in 4M urea. Incubation of human neutrophils with urea extract for 20 minutes caused a 600-fold increase in intracellular cAMP. Profound defects in superoxide generation were demonstrated not for only neutrophils but also for similarly treated human alveolar macrophages. The cAMP effect of Bordetella adenylate cyclase could be distinguished from that of pertussis toxin by (1) the rapid onset (minutes vs. hours), (2) the lack of any requirement for a hormone against, and (3) the recovery of Bordetella adenylate cyclase from treated, disrupted neutrophils. Subsequent studies have confirmed the action of Bordetella adenylate cyclase and extended its effects to a variety of other mammalian cell types.

The majority of adenylate cyclase enzyme activity in *B. pertussis* was associated with the cell wall of the organism. In fact, the addition of adenosine triphosphate (ATP) to intact, washed organisms resulted in the production of substantial amounts of cAMP. It was speculated that this enzyme activity might also signal the presence of *B. pertussis* organisms in human nasopharyngeal secretions. A series of experiments were undertaken to explore the possibility that adenylate cyclase assay may be a sensitive and specific way to detect *B. pertussis* infection in humans. The present method of diagnosis resulted.

THE PRIOR ART

In the United States, there are two standard approaches to the diagnosis of suspected *B. pertussis* infection. Most common is direct culture of the organism on a nutrient medium. While simple and highly specific, the culture technique is barely suitable owing to the prolonged incubations required and low sensitivity.

A newer technique involves direct demonstration of *B. pertussis* organisms in fixed nasal swab smears using anti-pertussis antibodies conjugated with a second fluorescent antibody. This technique is labor intensive and requires specially trained microscopists. Because of this, specificity and sensitivity are highly variable between facilities and even individual technicians.

Another developing technique focuses on serologic detection of a *B. pertussis* antibody response using an enzyme linked immunosorbent assay (ELISA) for anti-pertussis IgA, IgM and IgG in serum samples. The sensitivity of the ELISA in early *B. pertussis* infection remains to be established. These assays may be more sensitive than culture for early diagnosis of whooping cough in previously immunized and older patients. Such persons are capable of the prompt antibody response necessary to produce a positive result. Unfortunately, serological assays lack sensitivity in immunologically naive subjects, such as infants, and these are the patients most apt to suffer severe whooping cough infection. In fact, the major utility of serological testing is its use in the epidemiology of bacterial infections. A major disadvantage of the technique is the requirement of blood samples, especially since most of these will come from infants and children.

There is a pressing need for a simple rapid reliable diagnostic test for *B. pertussis* infection. The present invention is directed toward meeting that need. An assay has been developed which can rapidly detect *B. pertussis* on nasal swabs with surprising sensitivity. The assay is attractive because, like the ELISA, it uses an enzyme to amplify a small signal to a detectable level. Unlike the ELISA, however, the enzyme in this case is one present on the target. Thus a unique characteristic of the bacterium is exploited to advantage.

SUMMARY OF THE INVENTION

The diagnostic method according to this invention involves using the very high adenylate cyclase activity characteristic of Bordetella species as a specific diagnostic marker. Broadly stated, the method comprises assaying levels of cyclic adenosine monophosphate produced by adenylate cyclase present in afflicted patients. More particularly, the method comprises first obtaining a sample of nasopharyngeal secretions from a patient suspected of having a Bordetella disease, i.e., whooping cough. This sample is maintained in a nutrient medium pending assay. An adenylate cyclase assay is made by incubating the sample with an assay solution of adenosine triphosphate (ATP) and calmodulin (CaM) to generate adenosine 3',5'-cyclic monophosphate (cAMP). The assay solution also contains a further medium to encourage bacterial viability and replication and a radiolabeled cyclic adenosine monophosphate. Thereafter, the cAMP is measured by any of several known available methods and the existence or non-existence of Bordetella organisms is determined. This method provides greatly increased sensitivity and yields results in a fraction of the time required for culture.

To facilitate practice of the diagnostic method, a kit is preferably provided. The kit contains a nasal swab for the collection of secretions, a transport tube containing a nutrient medium, an assay solution, a binder solution, a developer column and a developer solution.

DETAILED DESCRIPTION OF THE PREFERRED EMBODIMENT

Bordetella is unique among bacteria because it possesses a soluble adenylate cyclase. This enzyme is the catalytic subunit of Bordetella adenylate cyclase toxin, a potent toxin demonstrated to exert profound effects on mammalian cell cAMP metabolism. The catalytic activity of Bordetella adenylate cyclase is impressive and can be stimulated many fold by the eukaryotic calcium binding protein, calmodulin. Experiments with Bordetella adenylate cyclase toxin have demonstrated that the majority of adenylate cyclase activity is loosely associated with the cell wall of the intact organism. Arrayed along the exterior, Bordetella adenylate cyclase serves as an excellent reporter of the organism's presence.

The present invention is directed to the detection of Bordetella infection, and particularly *B. pertussis* infection, by direct assay of adenylate cyclase activity in nasal swab specimens. The method comprises three steps: sample holding, adenylate cyclase assay, and measurement of cAMP.

Sample Holding

This step is designed to facilitate collection of viable bacteria in an outpatient clinic with subsequent transfer to a central laboratory for completion of the assay. No special equipment or sample handling is required.

A sample of nasopharyngeal secretions is collected on a calcium alginate nasal swab (such as Calgiswab, Type 1, Spectrum Diagnostics) by passage through the nostril of a patient suspected of having a Bordetella infection, all the way to the nasopharynx. The swab is preferably inserted sequentially into each nostril of the patient and advanced parallel to the hard palate with slow rotation until reaching the nasopharynx. The swab is transferred to a transport tube, such as a glass or plastic test tube, (13×100 mm, 16×120 mm, etc.) with a replaceable screw cap and containing a suitable volume, such as 1 to 10 ml (e.g. 5 ml), of a sterile transport charcoal medium. One such medium used in the experiments described herein is one-half strength Regan-Lowe medium (Regan, J. and Lowe, F., Enrichment medium for the isolation of Bordetella. J. Clin. Microbiol. 6:303–309, 1977), hereinafter described as Regan-Lowe medium.

Regan-Lowe transport medium (half strength) for 200 tubes containing 5 ml each is prepared as follows: Charcoal agar (25.5 g Difco 0894-01, or similar) is suspended in 1000 ml distilled water, boiled to dissolve, sterilized by autoclaving at 121° C. for 15 minutes and cooled to 50° C. Defibrinated blood of any kind (90 ml) is added. A cephalexin solution is prepared by mixing 0.0426 g of cephalexin powder (Eli Lilly) in 10 ml sterile distilled water, and adding this to the cooled charcoal agar. Final concentration of cephalexin equals 40 micrograms per ml. Although cephalexin is preferred, penicillin or methicillin may be used. The medium is stored at 4°–8° C.

Other suitable transport media include: Beef Heart Charcoal Agar (L. Mushalow, L. S. Sharpe, and L. L. Cohen, "Beef heart for the preparation of pertussis vaccines." Am. J. Publ. Health, 48:1466–1472 (1953):

| | |
|---|---|
| Bacto-peptone (Difco or similar) | 10 gm. |
| NaCl | 5 gm. |

| Soluble starch (Merck) | 10 gm. |
| Yeast extract (Difco) | 3.5 gm. |
| Agar-agar (Difco) | 2-4 gm. |
| H₂O to make 100 ml of solution | |

The tip of the swab is immersed in the semi-solid transport medium such that just the swab tip is covered by medium. The handle of the swab is cut with scissors to permit the transport tube to be re-capped. The transport tube is kept upright and at room temperature. Before use, the transport tube is stored at 4° C. to prolong the shelf life.

Adenylate Cyclase Assay

This step involves incubation of the sample with ATP and calmodulin to generate cAMP. The assay may be initiated at any time within 48 hours of specimen collection, usually at a central laboratory. The assay is carried out in a sterile solution which encourages bacterial viability (e.g. Stainer-Scholte medium, Stainer, D. W. and Scholte, M. J., A simple chemically defined medium for the production of phase I *Bordetella pertussis*. J. Gen. Microbiol. 63:211-220, 1971) supplemented with 200 nM to 5 mM (e.g. about 1 mM) adenosine triphosphate, 0.05 $\mu M$ to 5 $\mu M$ (e.g. about 0.1 $\mu M$) calmodulin, and radiolabeled cAMP in 1 nM to 200 nM concentration as appropriate for optimal sensitivity. Alternatively, any medium which permits the preservation and short term survival of Bordetella may be substituted. The assay solution is maintained frozen at about $-20°$ C. until the day of use. The assay solution is thawed. The cap is removed from the transport tube and a measured amount of 0.5 to 2 ml (e.g. about 1 ml) of assay medium is added on top of the transport medium. The swab is not removed. The tube is capped and incubated at 35°-37° C. upright with rotation for 24 to 48 hours.

The basal Stainer-Scholte liquid medium contains in grams per liter:

| Monosodium L-glutamate | 10.72 |
| L-proline | 0.24 |
| Sodium chloride | 2.50 |
| Potassium phosphate monobasic | 0.50 |
| Potassium chloride | 0.20 |
| Magnesium chloride hexahydrate | 0.10 |
| Calcium chloride dihydrate | 0.03 |
| Tris-base | 1.52 |

The pH of the solution is adjusted to 7.6 at room temperature. It is sterilized at 121.6° C. for 30 minutes and stored at 4° C. until use.

The supplement contains in grams per 100 ml:

| L-cystine | 0.40 |
| Ferrous sulfate 7H₂O | 0.10 |
| Ascorbic acid | 0.20 |
| Niacin | 0.04 |
| Reduced glutathione | 1.00 |

The L-cystine is dissolved in 12 ml of 1N HCl and the volume is brought to 100 ml with distilled water. The remaining ingredients are dissolved without heating. Five ml of supplement is added to 500 ml of basal medium.

cAMP Measurement

A variety of techniques is available for the determination of cAMP in solution. The present method for detecting Bordetella organisms is founded on the unique organismal adenylate cyclase which generates cAMP in the presence of Mg-adenosine triphosphate. The method is enabled by any of the available techniques. The following examples illustrate approaches to cAMP measurement:

(1) cAMP binding to mammalian protein kinase (PK). Radiolabeled (tritium, carbon-14, $^{125}I$, etc.) authentic cAMP is present in the reaction mixture as described above. This cAMP is allowed to compete with cAMP generated by organisms present on the nasal swab for binding to regulatory subunits of mammalian protein kinase (Brown et al, Saturation assay for cyclic AMP using endogenous binding protein. Adv. Cyclic Nucleotide Res 1972: 2: 25-40).

Protein kinase is prepared from fresh beef adrenal glands kept on ice until ready for use. As much fat and extraneous tissue as possible are removed from each gland. The glands are minced into fine pieces and mashed. A homogenization buffer is added in a volume 1.5× the weight (i.e. 1.5 ml/gm) and the mixture is homogenized in a blender. The composition of the buffer is:

| 0.25 M sucrose (mw = 342.3) | 85.57 g/l |
| 50 mM Tris HCl (mw = 158) | 7.9 g/l |
| 25 mM KCl (mw = 74.56) | 1.86 g/l |
| 5 mM MgCl₂ (mw = 203.3) | 1.02 g/l |
| pH = 7.4 at 4° C. | |

The homogenate is centrifuged at 2000 xg for 5 minutes and the supernatant fluid saved. This fluid is centrifuged at 5000 xg for 15 minutes, strained, aliquoted into 1 ml volumes and stored at $-20°$ C.

A solution of the protein kinase is added to the transport tube at completion of the adenylate cyclase assay and incubated for 90 minutes (60-360 minute range) to allow binding. Bound nucleotides are separated from the unbound by any of several techniques.

(a) Binding of free nucleotide to activated charcoal. Charcoal, e.g., Norit SG extra, will bind free nucleotides in solution but not those already bound to PK. Thus, charcoal (15-50 percent v/v in physiologic buffer (e.g., Tris, pH 7.0-7.6) is added to the reaction mixture and incubated for 20 minutes (10-60 minute range) in ice water bath. The charcoal is sedimented by low-speed centrifugation (e.g., 2000 xg for 30 minutes). An aliquot of the supernatant fluid is removed and the amount of PK-bound radiolabeled cAMP determined by liquid scintillation counting (LSC), if the label is tritium or carbon-14, or by Gamma radiation counting, if the label is $^{125}I$. In this situation, the radioactivity recovered is inversely proportional to the amount of cAMP generated by the organisms on the nasal swab specimen.

(b) Separation of bound nucleotide from free by gel permeation chromatography. In this method, bound and free nucleotides are separated on the basis of the molecular weight of the free nucleotide versus that of the protein-bound nucleotide complex. Following incubation with the PK solution, an aliquot of the reaction mixture is removed and placed on a developing column containing a gel-permeation medium with small pore size (e.g., Sephadex G-25, Pharmacia) which will admit the free nucleotide but exclude the protein-bound complex. The column is developed by adding an aliquot of water and collecting the effluent for determination of radioactivity as above. The volumes of the aliquot applied to the developing column are dependent upon the geometry of the column and determined by reference to the manufacturer's instructions. Here, again, the radioactivity recovered is inversely proportional to the cAMP generated by the organisms present on the sample swab.

(2) cAMP binding to anti-cAMP antibody.

cAMP assays in this class are similar to those above except that radiolabeled and authentic cAMP compete for binding to an anti-cAMP antibody. The potential advantages of these techniques include higher affinity between antibody and nucleotide and alternative approaches to the separation of bound and free nucleotide. The latter includes precipitation of the antibody-nucleotide complex with a second anti-antibody antibody and binding of the antibody-nucleotide complex to Staphylococcal Protein A. By these methods, the nucleotide-antibody complex is removed from solution and the remaining radioactivity (unbound) is proportional to the cAMP generated by the nasal swab organisms.

The exact technique employed for cAMP measurement will determine what constitutes a positive result. Thus, the assignment of clinical samples to positive and negative outcomes is dependent upon the almost limitless combination of conditions which can be employed.

The invention is further illustrated by the following examples:

EXAMPLE I

The following preliminary experiments were conducted with log-phase *B. pertussis* (University of Minnesota clinical isolate) growing in Stainer-Scholte liquid medium. Bacterial density was estimated with the NIH opacity standard, where an absorbence of 1.0 at 530 nM is equivalent to bacterial concentration of $10^{10}$ ml Preliminary experiments with radiochemically labeled water demonstrated that Calgiswabs had a reproducible water capacity of 7.9±1.4 μl and that equilibration was complete within 1 second of immersion. Thus, it is possible to coat the swabs with a known number of bacteria for subsequent assay. All assays were conducted in triplicate or quadruplicate and results averaged. Cyclic AMP was determined by a competitive protein binding assay described by Brown et al, supra.

Experiment #1

Regan-Lowe transport medium was inoculated with known numbers of *B. pertussis* and held at room temperature for 24 hours. The adenylate cyclase assay medium was added and cAMP determined after 24 and 48 hours of subsequent incubation at 35° C. The results in Table 1 show that as few as 100 bacteria per swab were readily detected after 24 hours of assay (48 hours from collection). Furthermore, continuation of the assay for an additional 24 hours resulted in further cAMP generation.

TABLE 1

Generation of cAMP from *B. pertussis* Coated Calcium Alginate Swabs

| Bacteria per Swab | cAMP pmol/100 μl sample 24 hours | 48 hours |
|---|---|---|
| 0 | <1 | <1 |
| $10^1$ | ND* | ND* |
| $10^2$ | 13.5 | >20 |
| $10^3$–$10^7$ | >20 | >20 |

*ND = Not Done

Experiment #2

The effect of the length of holding upon detection was investigated. Swabs were coated with bacteria from $10^2$/swab to $10^5$/swab and held in the Regan-Lowe transport medium for 0, 6, 12, 18 and 24 hours before addition of adenylate cyclase assay medium. The duration of holding had no effect on the ability to detect bacteria and significant cAMP was generated at each concentration and all time points. Thus, the holding time is not critical to the assay. Samples collected throughout the day in an outpatient clinic may be transported to the reference laboratory overnight and assayed the following day.

Experiment #3

The prototype method of this invention was compared to conventional culture of *B. pertussis* on full strength Regan-Lowe medium. Swabs were coated with bacteria and streaked on standard plates which were then incubated at 35° C. in 100 percent humidity. Plates were examined daily and the time to minimum detectable growth of *B. pertussis* recorded. For inocula of 100 to 10,000 cells growth could only be detected after 5 to 6 days in culture. Thus, positive results with the present method are achieved in less than one-third of the time of conventional culture.

Example II

In further studies, *B. pertussis* strain e9340 obtained from the American Type Culture Collection was used. Stock cultures were maintained frozen at −70° C. in sterile, defibrinated blood. Seed culture aliquots of 30–50 ml were stored at 4° C. for up to 14 days. To initiate a culture from frozen stock, 200 ul is added to 20 ml of modified Stainer-Scholte medium containing 20 mg Dowex 1-X8 (Bio-Rad, Richmond, CA) and incubated at 37° C. with rotation (200 rpm). The culture is maintained in log-phase growth by serial inoculation of aliquots into fresh Stainer-Scholte medium without Dowex. Seed cultures are inoculated into 400–500 ml of Stainer-Scholte medium. By the timed addition of fresh medium, the culture is expanded to any desired volume. Bacterial concentration is estimated by comparison to the NIH opacity standard (supra).

Calcium alginate swabs (Calgiswab, Type 1) were immersed for 5 seconds in a bacterial suspension of known concentration and then transferred to sterile, room temperature, 16×120 mm screw cap test tubes containing 5 ml each of one-half strength Bacto charcoal agar (Difco) with 40 ug/ml cephalexin. Studies with tritiated cAMP in deionized water determined the absorbency of the swabs to be 7.9±1.4 ul with complete equilibration in 1 second. For simplicity the absorbency was assumed to be 10 ul per swab. Nasal swabs from normal volunteers were introduced through the nares, advanced with slow rotation to the posterior wall of the nasopharynx, withdrawn and placed in the transport medium.

The inoculated transport tubes were held at room temperature for 0 to 24 hours. To initiate the production of cAMP, 1 ml of Stainer-Scholte medium containing 1 mM ATP (Sigma, St. Louis, MO), 0.1 uM bovine brain calmodulin (Sigma), and 40 ug/ml cephalexin was added. The tubes were then incubated at 37° C. with rotation at 200 rpm. Following incubation, the tubes were centrifuged at 2000 xg for 10 min and cAMP in 100 ul of supernatant fluid was determined by a competitive protein binding assay (supra). The effective range of the assay is from 1 pmol to 20 pmol cAMP/100 ul sample volume.

Experiment #1

Calcium alginate swabs were coated in triplicate with known numbers of $B.$ $pertussis$ from $10^2$ to $10^7$/swab and placed in room temperature transport medium for a 24 hour holding period. ATP containing Stainer-Scholte medium was then added and the samples were incubated for an additional 24 hours at 37° C. prior to assay for cAMP. No cAMP was detected in tubes without $B.$ $pertussis$, but tubes with only 100 organisms per swab generated $13.5 \pm 6$ pmol cAMP/100 ul sample volume ($t=4.0$, $p<0.02$). In this experiment, all tubes with $10^3$ to $10^7$ organisms/swab produced more than 20 pmol cAMP/100 ul sample volume.

Table 2 presents the combined results of 14 different experiments where $B.$ $pertussis$ coated swabs were assayed for adenylate cyclase activity. These results show that no false positives were recorded and yet only 2 false negatives (15.4 percent) occurred in 13 experiments where swabs were coated with 100 organisms.

TABLE 2

| | cAMP generation from $B.$ $pertussis$ containing calcium alginate swabs in 14 experiments | | | |
|---|---|---|---|---|
| | pmol cAMP/100 ul sample/24 hours | | | |
| $B.$ $pertussis$ (organisms/swab)* | <1 | 1-10 | 11-20 | >20 |
| | (number of experiments) | | | |
| 0 | 14 | 0 | 0 | 0 |
| $10^2$ | 2 | 8 | 1 | 2 |
| $10^3$ | 1 | 8 | 1 | 4 |
| $10^4$ | 0 | 3 | 3 | 7 |
| $10^5$ | 0 | 0 | 0 | 5 |
| $10^6$ | 0 | 0 | 0 | 3 |
| $10^7$ | 0 | 0 | 0 | 3 |

*For each concentration of $B.$ $pertussis$ v. 0 organism, $P < 0.001$ by Mann-Whitney U test.

Experiment #2

To examine a more realistic model, nasal swabs were obtained from healthy adults and assayed for adenylate cyclase activity with or without the addition of $B.$ $pertussis$ organisms. The results (Table 3) show that no adenylate cyclase activity was detected in normal nasopharyngeal secretions. Further, the normal secretions did not impair the sensitivity of the assay when carried out with added $B.$ $pertussis$.

TABLE 3

| cAMP generation from calcium alginate nasal swabs of volunteers with and without added $B.$ $pertussis$ organisms. | | |
|---|---|---|
| added organisms per swab | n | pmol cAMP/100 ul sample per 24 hours |
| 0 | 4 | <1 |
| $10^2$ | 3 | 3, 6.1, 5.3 |

TABLE 3-continued

| cAMP generation from calcium alginate nasal swabs of volunteers with and without added $B.$ $pertussis$ organisms. | | |
|---|---|---|
| added organisms per swab | n | pmol cAMP/100 ul sample per 24 hours |
| $10^3$ | 2 | 18.1, 6.7 |
| $10^4$ | 3 | 7.1, 17.8, 16.9 |
| $10^5$ | 3 | >20 |

*for $10^2$ organisms v. 0 organisms, $t = 6.18$, $p < 0.01$.

Example III

In clinical whooping cough, other respiratory pathogens may be co-isolated with $B.$ $pertussis$. In one study, the most common isolates were $Haemophilus$ $influenzae$ (4.8 percent), Streptococcus aureus (2.7 percent), $E.$ $coli$ (2.1 percent) and $Streptococcus$ $pyogenes$ (2.1 percent). An investigation was undertaken of the potential interference of these organisms in the assay.

$H.$ $influenzae$ stock cultures were maintained on GC medium (Difco, Detroit, MI) at 25° C. Liquid suspension cultures for experiments were prepared by inoculation of Tryptic Soy Broth (Gibco, Madison, WI) supplemented with 6 percent (v/v) IsoVitalex (BBL Microbiological Systems, Cockeysville, MD), $S.$ $aureus$ were maintained on Blood Agar (Difco) and in Nutrient Broth (Difco), respectively. Solid phase $E.$ $coli$ were grown on Nutrient Agar (Difco) and suspension cultures prepared in Brain Heart Infusion Broth (Difco). $S.$ $pyogenes$ cultures were carried out on Blood Agar and in Todd-Hewitt Broth (Difco). It was found (Table 4) that none of the tested organisms in pure culture produced detectable cAMP. More importantly, when admixed with $B.$ $pertussis$, even to equal proportions, none of the organisms tested blocked the production of cAMP (Table 4).

TABLE 4

| cAMP generation from calcium alginate swabs containing $B.$ $pertussis$ and co-isolating bacteria. | | |
|---|---|---|
| organisms/swab | | pmol cAMP/100 ul Sample per 24 hours* |
| $B.$ $pertussis$ | $H.$ $influenzae$ | |
| $10^3$ | 0 | >20 |
| $10^3$ | 10 | 8.5 |
| $10^3$ | $10^2$ | 13 |
| $10^3$ | $10^3$ | 12 |
| 0 | $10^7$ | <1 |
| $B.$ $pertussis$ | $S.$ $pyogenes$ | |
| $10^3$ | 0 | >20 |
| $10^3$ | 10 | 18 |
| $10^3$ | $10^2$ | 17 |
| $10^3$ | $10^3$ | >20 |
| 0 | $10^7$ | <1 |
| $B.$ $pertussis$ | $S.$ $aureus$ | |
| $10^3$ | 0 | >20 |
| $10^3$ | 10 | 11 |
| $10^3$ | $10^2$ | >20 |
| $10^3$ | $10^3$ | 12 |
| 0 | $10^7$ | <1 |
| $B.$ $pertussis$ | $E.$ $coli$ | |
| $10^3$ | 0 | >20 |
| $10^3$ | 10 | 8.8 |
| $10^3$ | $10^2$ | 8.0 |
| $10^3$ | $10^3$ | 8.3 |
| 0 | $10^7$ | <1 |

*Average of triplicate assays

For convenience in making diagnosis of whooping cough in suspected patients, a kit for the detection of $B.$ $pertussis$ is preferably provided for use in physicians' offices, outpatient clinics, and the like. The kit consists of six components: (1) a sterile calcium alginate nasal swab; (2) a glass or plastic transport tube with a replaceable cap, containing a suitable volume of a sterile transport medium; (3) a sterile assay solution of support medium supplemented with adenosine triphosphate, calmodulin, and radiolabeled cAMP in appropriate concentrations for optimal sensitivity; (4) a buffered binder solution containing an appropriate concentration of a cAMP binding protein; (5) a pre-packed developer column containing an appropriate matrix for adsorption of the cAMP binding protein in the binder solution; and (6) a buffer developer solution. The kit is furnished with instructions for use, as already described.

It is apparent that many modifications and variations of this invention as hereinbefore set forth may be made without departing from the spirit and scope thereof. The specific embodiments described are given by way of example only, and the invention is limited only by the terms of the appended claims.

We claim:

1. A method for the diagnosis of Bordetella diseases in their earliest stages when bacteria in the nasopharyngeal secretions of the suspected patient are present in numbers as few as 100 bacteria per nasal swab inserted into the nostrils of the patient and removed, which method comprises assaying levels of cyclic adenosine monophosphate produced by extra-cellular adenylate cyclase present in patients afflicted with Bordetella diease by:
   (A) obtaining a specimen of nasopharyngeal secretions by inserting a nasal swab into the nostrils of a patient suspected of having a Bordetella disease and removing,
   (B) maintaining the specimen in a nutrient medium pending assay,
   (C) adding an assay solution of adenosine triphosphate, calmodulin and radiolabeled cyclic adenosine monophosphate to the specimen,
   (D) incubating the specimen and assay solution for about 24 to 48 hours at about 35°-37° C., to develop cyclic adenosine monophosphate from any Bordetella organisms present in the specimen, and
   (E) detecting Bordetella organisms by measuring cyclic adenosine monophosphate developed.

2. A method according to claim 1 wherein said swab contains calcium alginate.

3. A method according to claim 2 wherein said maintaining of the specimen is preformed in a transport tube having a removable cap and said swab is maintained in said tube to maintain Bordetella organisms in the specimens from patients suspected of having Bordetella disease.

4. A method according to claim 3 wherein the nasopharyngeal specimen is maintained in one-half strength charcoal medium.

5. A method according to claim 1 wherein the assay solution contains a further nutrient medium to encourage bacterial viability and replication.

6. A method according to claim 5 wherein said further nutrient medium is Stainer-Scholte medium.

7. A method according to claim 1 wherein cyclic adenosine monophosphate is measured by:
   (A) adding a buffered solution of cyclic adenosine monophosphate binding protein to the incubated assay solution,
   (B) transferring the solution to a developer column containing a matrix for adsoption of the binding protein,
   (C) eluting the absorbed binding protein and bound cyclic adenosine monophosphate with a buffered developer solution,
   (D) adding an aqueous scintillation solution and counting the cyclic adenosine monophosphate generated.

8. A method for the diagnosis of whooping cough in its earliest stage when bacteria in the nasopharyngeal secretions of the suspected patient are present in numbers as few as 100 bacteria per nasal swab inserted into the nostrils of the patient and removed, which method comprises:
   (A) obtaining a specimen of nasopharyngeal secretions from a patient suspected of having whooping cough by inserting a nasal swab into the nostrils of the patient and removing,
   (B) maintaining the specimen in a nutrient medium pending assay,
   (C) adding an assay solution of adenosine triphosphate, calmodulin and radiolabeled cyclic adenosine monophosphate to the specimen,
   (D) incubating the specimen and assay solution for about 24 to 48 hours at about 35°-37° C., to develop extra-cellularly produced cyclic adenosine monophosphate from any Bordetella pertussis organisms present in the specimen,
   (E) adding a buffered solution of cyclic adenosine monophosphate binding protein to the incubated assay solution,
   (F) transferring the solution to a developer column containing a matrix for adsorption of the binding protein,
   (G) eluting the adsorbed binding protein and bound cyclic adenosine monophosphate with a buffered developer solution,
   (H) adding an aqueous scintillation solution to the eluted solution,
   (I) counting the cyclic adenosine monophosphate generated, and
   (J) determining the presence of B. pertussis from the presence of cyclic adenosine monophosphate.

9. A method according to claim 8 wherein said swab contains calcium alginate.

10. A method according to claim 9 wherein said maintaining of the speciman is preformed in a transport tube having a removable cap and said swab is maintained in said tube to maintain Bordetella organisms in the specimens from patients suspected of having Bordetella disease.

11. A method according to claim 10 wherein the nasopharyngeal specimen is maintained in one-half strength charcoal medium.

12. A method according to claim 8 wherein the assay solution contains a further nutrient medium to encourage bacterial viability and replication.

13. A method according to claim 12 wherein said further medium is Stainer-Scholte medium.

14. Means for facilitating the diagnosis of Bordetella diseases in their earliest stages, when bacteria in the nasopharyngeal secretions of the suspected patient are present in numbers as few as 100 bacteria per nasal swab inserted into the nostrils of the patient and removed, by assaying levels of cyclic adenosine monophosphate produced by extracellular adenylate cyclase present in patients afflicted with Bordetella disease, which means comprises:
   (A) a sterile nasal swab for the collection of nasopharyngeal secretions from a suspected whooping cough patient wherein said swab is a calcium alginate swab, and
(B) an elongated storage and transport tube for receiving said swab wherein said tube is glass or plastic and said tube
  (1) having a replaceable end closure, and
  (2) containing a sterile nutrient medium for the isolation of Bordetella organisms,
(C) a sterile assay solution for addition to said transport tube which includes:
  (1) Stainer-Scholte medium,
  (2) adenosine triphosphate,
  (3) calmodulin, and
  (4) radiolabeled cyclic adenosine monophosphate,
(D) a buffered binder solution containing a binding protein for cyclic adenosine monophosphate,
(E) a pre-packed developer column containing a matrix for adsorption of said binding protein, and
(F) a buffered developer solution for eluting adsorbed binding protein and cyclic adenosine monophosphate from said column.

* * * * *